US007288633B2

(12) United States Patent
Lyman et al.

(10) Patent No.: US 7,288,633 B2
(45) Date of Patent: Oct. 30, 2007

(54) MODIFIED HUMAN THYMIC STROMAL LYMPHOPOIETIN

(75) Inventors: Stewart D. Lyman, Seattle, WA (US); Kirk P. Van Ness, Seattle, WA (US); Raymond J. Paxton, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 256 days.

(21) Appl. No.: 10/202,699

(22) Filed: Jul. 23, 2002

(65) Prior Publication Data

US 2007/0218523 A1 Sep. 20, 2007

Related U.S. Application Data

(60) Provisional application No. 60/307,345, filed on Jul. 23, 2001.

(51) Int. Cl.
*C07K 14/475* (2006.01)
*C07K 14/52* (2006.01)

(52) U.S. Cl. ....................................... 530/351; 530/402

(58) Field of Classification Search ..................... None
See application file for complete search history.

(56) References Cited

U.S. PATENT DOCUMENTS 6,555,520 B2 4/2003 Sims et al.

FOREIGN PATENT DOCUMENTS

WO WO 00/29581 5/2000

OTHER PUBLICATIONS

MIkayama et al. Proc. Natl. Acad. Sci. USA vol. 90, pp. 10056-10060, 1993.*

Voet et al. Biochemistry. John Wiley & Sons, Inc., pp. 126-128 and 228-234.*
Levin SD, et al., "Thymic Stromal Lymphopoietin: A Cytokine that Promotes the Development of IgM+B Cells in Vitro and Signals Via a Novel Mechanism," *J Immunology*, 162:677-683, 1999.
Pandey A, et al., "Cloning of a receptor subunit required for signaling by thymic stromal lymphopoietin," *Nature Immunology*, 1(1):59-64, Jul. 2000.
Park LS, et al., "Cloning of the Murine Thymic Stromal Lymphopoietin (TSLP) Receptor: Formation of a Functional Heteromeric Complex Requires Interleukin 7 Receptor," *J Experimental Medicine* 192(5):659-669, Sep. 2000.

Reche PA, et al., "Human Thymic Stromal Lymphopoietin Preferentially Stimulates Myeloid Cells," *J of Immunology* 167:336-343,2001.

Sims JE, et al., "Molecular Cloning and Biological Characterizations of a Novel Murine Lymphoid Growth Factor," *J. Experimental Medicine* 192(5):671-680, Sep. 2000.
Hosaka, et al., "Arg-X-Lys/Arg-Arg Motif as a signal for precursor cleavage catalyzed by furin within the constitutive secretory pathway," *J. Biol. Chem.* 266 (19), 12127-12130, 1991.

* cited by examiner

*Primary Examiner*—Prema Mertz
(74) *Attorney, Agent, or Firm*—Thomas J. Wrona

(57) ABSTRACT

Modified, furin resistant human TSLP polypeptides and polynucleotides encoding the modified human TSLP polypeptides are provided. Pharmaceutical compositions, B and T cell activation agents, assays and methods of use are also described.

7 Claims, No Drawings

SEQUENCE LISTING

<160> NUMBER OF SEQ ID NOS: 22

<210> SEQ ID NO 1
<211> LENGTH: 1125
<212> TYPE: DNA
<213> ORGANISM: Mus musculus
<220> FEATURE:
<221> NAME/KEY: CDS
<222> LOCATION: (18)..(440)
<223> OTHER INFORMATION:

<400> SEQUENCE: 1

```
cacgttcagg cgacagc atg gtt ctt ctc agg agc ctc ttc atc ctg caa          50
                   Met Val Leu Leu Arg Ser Leu Phe Ile Leu Gln
                    1               5                  10 gta cta gta cgg atg ggg cta act tac aac ttt tct aac tgc aac ttc         98
Val Leu Val Arg Met Gly Leu Thr Tyr Asn Phe Ser Asn Cys Asn Phe
             15                  20                  25 acg tca att acg aaa ata tat tgt aac ata att ttt cat gac ctg act        146
Thr Ser Ile Thr Lys Ile Tyr Cys Asn Ile Ile Phe His Asp Leu Thr
         30                  35                  40 gga gat ttg aaa ggg gct aag ttc gag caa atc gag gac tgt gag agc        194
Gly Asp Leu Lys Gly Ala Lys Phe Glu Gln Ile Glu Asp Cys Glu Ser
     45                  50                  55 aag cca gct tgt ctc ctg aaa atc gag tat tat act ctc aat cct atc        242
Lys Pro Ala Cys Leu Leu Lys Ile Glu Tyr Tyr Thr Leu Asn Pro Ile
 60                  65                  70                  75 cct ggc tgc cct tca ctc ccc gac aaa aca ttt gcc cgg aga aca aga        290
Pro Gly Cys Pro Ser Leu Pro Asp Lys Thr Phe Ala Arg Arg Thr Arg
                 80                  85                  90 gaa gcc ctc aat gac cac tgc cca ggc tac cct gaa act gag aga aat        338
Glu Ala Leu Asn Asp His Cys Pro Gly Tyr Pro Glu Thr Glu Arg Asn
             95                 100                 105 gac ggt act cag gaa atg gca caa gaa gtc caa aac atc tgt ctg aat        386
Asp Gly Thr Gln Glu Met Ala Gln Glu Val Gln Asn Ile Cys Leu Asn
        110                 115                 120 caa acc tca caa att cta aga ttg tgg tat tcc ttc atg caa tct cca        434
Gln Thr Ser Gln Ile Leu Arg Leu Trp Tyr Ser Phe Met Gln Ser Pro
    125                 130                 135 gaa taa aattagcttt cagcttctgc tatgaaaatc tctatcttgg ttttagtgga        490
Glu
140 cagaatacta aggtgtgac acttagagga ccactggtgt ttattcttta attacagaag      550 ggattcttaa cttattttt ggcatatcgc tttttcagt ataggtgctt taaatgggaa       610 atgagcaata gaccgttaat ggaaatatct gtactgttaa tgaccagctt ctgagaagtc    670 tttctcacct ccctgcaca caccttactc tagggcaaac ctaactgtag taggaagaga    730 attgaaagta gaaaaaaaa ttaaaaccaa tgacagcatc taaaccctgt ttaaaaggca    790 aggattttc tacctgtaat gattcttcta acattcctat gctaagattt taccaaagaa     850 gaaaatgaca gttcgggcag tcactgccat gatgaggtgg tctgaaagaa gcttgtggaa    910 tctgggagaa actgctgaga tcatattgca aatccagctg tcaaagggtt cagacccagg    970 acagtacaat tcgtgagcag atctcaagag ccttgcacat ctacgagata tatatttaaa   1030 gttgtagata atgaatttct aatttatttt gtgagcactt ttggaaatat acatgctact   1090 ttgtaatgaa tacattgctg aataaagtaa ttctc                              1125
```

-continued

<210> SEQ ID NO 2
<211> LENGTH: 140
<212> TYPE: PRT
<213> ORGANISM: Mus musculus

<400> SEQUENCE: 2

```
Met Val Leu Leu Arg Ser Leu Phe Ile Leu Gln Val Leu Val Arg Met
1               5                   10                  15

Gly Leu Thr Tyr Asn Phe Ser Asn Cys Asn Phe Thr Ser Ile Thr Lys
            20                  25                  30

Ile Tyr Cys Asn Ile Ile Phe His Asp Leu Thr Gly Asp Leu Lys Gly
        35                  40                  45

Ala Lys Phe Glu Gln Ile Glu Asp Cys Glu Ser Lys Pro Ala Cys Leu
    50                  55                  60

Leu Lys Ile Glu Tyr Tyr Thr Leu Asn Pro Ile Pro Gly Cys Pro Ser
65                  70                  75                  80

Leu Pro Asp Lys Thr Phe Ala Arg Arg Thr Arg Glu Ala Leu Asn Asp
                85                  90                  95

His Cys Pro Gly Tyr Pro Glu Thr Glu Arg Asn Asp Gly Thr Gln Glu
            100                 105                 110

Met Ala Gln Glu Val Gln Asn Ile Cys Leu Asn Gln Thr Ser Gln Ile
        115                 120                 125

Leu Arg Leu Trp Tyr Ser Phe Met Gln Ser Pro Glu
    130                 135                 140
```

<210> SEQ ID NO 3
<211> LENGTH: 743
<212> TYPE: DNA
<213> ORGANISM: Homo sapiens
<220> FEATURE:
<221> NAME/KEY: CDS
<222> LOCATION: (200)..(679)
<223> OTHER INFORMATION:

<400> SEQUENCE: 3

```
gcagccagaa agctctggag catcagggag actccaactt aaggcaacag catgggtgaa      60
taagggcttc ctgtggactg caatgagag caaaacctg gtgcttgagc actggcccct       120
aaggcaggcc ttacagatct cttacactcg tggtgggaag agtttagtgt gaaactgggg     180
tggaattggg tgtccacgt atg ttc cct ttt gcc tta cta tat gtt ctg tca      232
                      Met Phe Pro Phe Ala Leu Leu Tyr Val Leu Ser
                      1               5                   10 gtt tct ttc agg aaa atc ttc atc tta caa ctt gta ggg ctg gtg tta      280
Val Ser Phe Arg Lys Ile Phe Ile Leu Gln Leu Val Gly Leu Val Leu
            15                  20                  25 act tac gac ttc act aac tgt gac ttt gag aag att aaa gca gcc tat      328
Thr Tyr Asp Phe Thr Asn Cys Asp Phe Glu Lys Ile Lys Ala Ala Tyr
        30                  35                  40 ctc agt act att tct aaa gac ctg att aca tat atg agt ggg acc aaa      376
Leu Ser Thr Ile Ser Lys Asp Leu Ile Thr Tyr Met Ser Gly Thr Lys
    45                  50                  55 agt acc gag ttc aac aac acc gtc tct tgt agc aat cgg cca cat tgc      424
Ser Thr Glu Phe Asn Asn Thr Val Ser Cys Ser Asn Arg Pro His Cys
60                  65                  70                  75 ctt act gaa atc cag agc cta acc ttc aat ccc acc gcc ggc tgc gcg      472
Leu Thr Glu Ile Gln Ser Leu Thr Phe Asn Pro Thr Ala Gly Cys Ala
                80                  85                  90 tcg ctc gcc aaa gaa atg ttc gcc atg aaa act aag gct gcc tta gct      520
Ser Leu Ala Lys Glu Met Phe Ala Met Lys Thr Lys Ala Ala Leu Ala
            95                  100                 105
```

```
atc tgg tgc cca ggc tat tcg gaa act cag ata aat gct act cag gca      568
Ile Trp Cys Pro Gly Tyr Ser Glu Thr Gln Ile Asn Ala Thr Gln Ala
        110                 115                 120 atg aag aag agg aga aaa agg aaa gtc aca acc aat aaa tgt ctg gaa      616
Met Lys Lys Arg Arg Lys Arg Lys Val Thr Thr Asn Lys Cys Leu Glu
125                 130                 135 caa gtg tca caa tta caa gga ttg tgg cgt cgc ttc aat cga cct tta      664
Gln Val Ser Gln Leu Gln Gly Leu Trp Arg Arg Phe Asn Arg Pro Leu
140                 145                 150                 155 ctg aaa caa cag taa accatctta ttatggtcat atttcacagc ccaaaataaa       719
Leu Lys Gln Gln tcatctttat taagtaaaaa aaaa                                           743

<210> SEQ ID NO 4
<211> LENGTH: 159
<212> TYPE: PRT
<213> ORGANISM: Homo sapiens

<400> SEQUENCE: 4

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 5
<211> LENGTH: 15
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 5 agg aga aaa agg aaa                                                   15
Arg Arg Lys Arg Lys
1               5

<210> SEQ ID NO 6
<211> LENGTH: 5
<212> TYPE: PRT
<213> ORGANISM: Homo sapiens

<400> SEQUENCE: 6
```

Arg Arg Lys Arg Lys
1               5

<210> SEQ ID NO 7
<211> LENGTH: 15
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 7 aga aaa agg aaa gtc                                               15
Arg Lys Arg Lys Val
1               5

<210> SEQ ID NO 8
<211> LENGTH: 5
<212> TYPE: PRT
<213> ORGANISM: Homo sapiens

<400> SEQUENCE: 8

Arg Lys Arg Lys Val
1               5

<210> SEQ ID NO 9
<211> LENGTH: 743
<212> TYPE: DNA
<213> ORGANISM: Homo sapiens
<220> FEATURE:
<221> NAME/KEY: CDS
<222> LOCATION: (200)..(679)
<223> OTHER INFORMATION:
<220> FEATURE:
<221> NAME/KEY: misc_feature
<222> LOCATION: (200)..(679)
<223> OTHER INFORMATION: "nnn" is a codon encoding any amino acid that
      is not Arg or Lys.
<220> FEATURE:
<221> NAME/KEY: misc_feature
<222> LOCATION: (200)..(679)
<223> OTHER INFORMATION: "Xaa" is not Arg or Lys; "nnn" does not encode
      Arg or Lys.

<400> SEQUENCE: 9
gcagccagaa agctctggag catcagggag actccaactt aaggcaacag catgggtgaa        60
taagggcttc ctgtggactg gcaatgagag gcaaaacctg gtgcttgagc actggccccct      120 aaggcaggcc ttacagatct cttacactcg tggtgggaag agtttagtgt gaaactgggg       180
tggaattggg tgtccacgt atg ttc cct ttt gcc tta cta tat gtt ctg tca        232
                    Met Phe Pro Phe Ala Leu Leu Tyr Val Leu Ser
                     1               5                  10 gtt tct ttc agg aaa atc ttc atc tta caa ctt gta ggg ctg gtg tta        280
Val Ser Phe Arg Lys Ile Phe Ile Leu Gln Leu Val Gly Leu Val Leu
            15                  20                  25 act tac gac ttc act aac tgt gac ttt gag aag att aaa gca gcc tat        328
Thr Tyr Asp Phe Thr Asn Cys Asp Phe Glu Lys Ile Lys Ala Ala Tyr
        30                  35                  40 ctc agt act att tct aaa gac ctg att aca tat atg agt ggg acc aaa        376
Leu Ser Thr Ile Ser Lys Asp Leu Ile Thr Tyr Met Ser Gly Thr Lys
    45                  50                  55 agt acc gag ttc aac aac acc gtc tct tgt agc aat cgg cca cat tgc        424
Ser Thr Glu Phe Asn Asn Thr Val Ser Cys Ser Asn Arg Pro His Cys
60                  65                  70                  75

```
ctt act gaa atc cag agc cta acc ttc aat ccc acc gcc ggc tgc gcg      472
Leu Thr Glu Ile Gln Ser Leu Thr Phe Asn Pro Thr Ala Gly Cys Ala
            80                  85                  90 tcg ctc gcc aaa gaa atg ttc gcc atg aaa act aag gct gcc tta gct      520
Ser Leu Ala Lys Glu Met Phe Ala Met Lys Thr Lys Ala Ala Leu Ala
        95                 100                 105 atc tgg tgc cca ggc tat tcg gaa act cag ata aat gct act cag gca      568
Ile Trp Cys Pro Gly Tyr Ser Glu Thr Gln Ile Asn Ala Thr Gln Ala
        110                 115                 120 atg aag aag nnn nnn nnn nnn nnn gtc aca acc aat aaa tgt ctg gaa      616
Met Lys Lys Xaa Xaa Xaa Xaa Xaa Val Thr Thr Asn Lys Cys Leu Glu
        125                 130                 135 caa gtg tca caa tta caa gga ttg tgg cgt cgc ttc aat cga cct tta      664
Gln Val Ser Gln Leu Gln Gly Leu Trp Arg Arg Phe Asn Arg Pro Leu
140                 145                 150                 155 ctg aaa caa cag taa accatcttta ttatggtcat atttcacagc ccaaaataaa      719
Leu Lys Gln Gln
tcatctttat taagtaaaaa aaaa                                           743

<210> SEQ ID NO 10
<211> LENGTH: 159
<212> TYPE: PRT
<213> ORGANISM: Homo sapiens
<220> FEATURE:
<221> NAME/KEY: misc_feature
<222> LOCATION: (127)..(127)
<223> OTHER INFORMATION: The 'Xaa' at location 127 stands for any amino
      acid except Lys or Arg.
<220> FEATURE:
<221> NAME/KEY: misc_feature
<222> LOCATION: (128)..(128)
<223> OTHER INFORMATION: The 'Xaa' at location 128 stands for any amino
      acid except Lys or Arg.
<220> FEATURE:
<221> NAME/KEY: misc_feature
<222> LOCATION: (129)..(129)
<223> OTHER INFORMATION: The 'Xaa' at location 129 stands for any amino
      acid except Lys or Arg.
<220> FEATURE:
<221> NAME/KEY: misc_feature
<222> LOCATION: (130)..(130)
<223> OTHER INFORMATION: The 'Xaa' at location 130 stands for any amino
      acid except Lys or Arg.
<220> FEATURE:
<221> NAME/KEY: misc_feature
<222> LOCATION: (131)..(131)
<223> OTHER INFORMATION: The 'Xaa' at location 131 stands for any amino
      acid except Lys or Arg.
<220> FEATURE:
<221> NAME/KEY: misc_feature
<222> LOCATION: (200)..(679)
<223> OTHER INFORMATION: "nnn"  is a codon encoding any amino acid that
      is not Arg or Lys.
<220> FEATURE:
<221> NAME/KEY: misc_feature
<222> LOCATION: (200)..(679)
<223> OTHER INFORMATION: "Xaa" is not Arg or Lys; "nnn" does not encode
      Arg or Lys.

<400> SEQUENCE: 10

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60
```

-continued

```
Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Xaa Xaa
        115                 120                 125

Xaa Xaa Xaa Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155
```

<210> SEQ ID NO 11
<211> LENGTH: 731
<212> TYPE: DNA
<213> ORGANISM: Homo sapiens
<220> FEATURE:
<221> NAME/KEY: CDS
<222> LOCATION: (200)..(667)
<223> OTHER INFORMATION:

<400> SEQUENCE: 11

```
gcagccagaa agctctggag catcagggag actccaactt aaggcaacag catgggtgaa      60
taagggcttc ctgtggactg caatgagag gcaaaacctg gtgcttgagc actggcccct     120
aaggcaggcc ttacagatct cttacactcg tggtgggaag agtttagtgt gaaactgggg     180
tggaattggg tgtccacgt atg ttc cct ttt gcc tta cta tat gtt ctg tca     232
                    Met Phe Pro Phe Ala Leu Leu Tyr Val Leu Ser
                      1               5                  10 gtt tct ttc agg aaa atc ttc atc tta caa ctt gta ggg ctg gtg tta     280
Val Ser Phe Arg Lys Ile Phe Ile Leu Gln Leu Val Gly Leu Val Leu
             15                  20                  25 act tac gac ttc act aac tgt gac ttt gag aag att aaa gca gcc tat     328
Thr Tyr Asp Phe Thr Asn Cys Asp Phe Glu Lys Ile Lys Ala Ala Tyr
         30                  35                  40 ctc agt act att tct aaa gac ctg att aca tat atg agt ggg acc aaa     376
Leu Ser Thr Ile Ser Lys Asp Leu Ile Thr Tyr Met Ser Gly Thr Lys
     45                  50                  55 agt acc gag ttc aac aac acc gtc tct tgt agc aat cgg cca cat tgc     424
Ser Thr Glu Phe Asn Asn Thr Val Ser Cys Ser Asn Arg Pro His Cys
 60                  65                  70                  75 ctt act gaa atc cag agc cta acc ttc aat ccc acc gcc ggc tgc gcg     472
Leu Thr Glu Ile Gln Ser Leu Thr Phe Asn Pro Thr Ala Gly Cys Ala
             80                  85                  90 tcg ctc gcc aaa gaa atg ttc gcc atg aaa act aag gct gcc tta gct     520
Ser Leu Ala Lys Glu Met Phe Ala Met Lys Thr Lys Ala Ala Leu Ala
         95                 100                 105 atc tgg tgc cca ggc tat tcg gaa act cag ata aat gct act cag gca     568
Ile Trp Cys Pro Gly Tyr Ser Glu Thr Gln Ile Asn Ala Thr Gln Ala
    110                 115                 120 atg aag aag agg gtc aca acc aat aaa tgt ctg gaa caa gtg tca caa     616
Met Lys Lys Arg Val Thr Thr Asn Lys Cys Leu Glu Gln Val Ser Gln
125                 130                 135 tta caa gga ttg tgg cgt cgc ttc aat cga cct tta ctg aaa caa cag     664
Leu Gln Gly Leu Trp Arg Arg Phe Asn Arg Pro Leu Leu Lys Gln Gln
140                 145                 150                 155 taa accatcttta ttatggtcat atttcacagc ccaaaataaa tcatctttat          717
taagtaaaaa aaaa                                                    731
```

-continued

<210> SEQ ID NO 12
<211> LENGTH: 155
<212> TYPE: PRT
<213> ORGANISM: Homo sapiens

<400> SEQUENCE: 12

```
Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Val
        115                 120                 125

Thr Thr Asn Lys Cys Leu Glu Gln Val Ser Gln Leu Gln Gly Leu Trp
130                 135                 140

Arg Arg Phe Asn Arg Pro Leu Leu Lys Gln Gln
145                 150                 155
```

<210> SEQ ID NO 13
<211> LENGTH: 728
<212> TYPE: DNA
<213> ORGANISM: Homo sapiens
<220> FEATURE:
<221> NAME/KEY: CDS
<222> LOCATION: (200)..(664)
<223> OTHER INFORMATION:

<400> SEQUENCE: 13

```
gcagccagaa agctctggag catcagggag actccaactt aaggcaacag catgggtgaa      60
taagggcttc ctgtggactg caatgagag caaaacctg gtgcttgagc actggcccct       120
aaggcaggcc ttacagatct cttacactcg tggtgggaag agtttagtgt gaaactgggg     180
tggaattggg tgtccacgt atg ttc cct ttt gcc tta cta tat gtt ctg tca     232
                    Met Phe Pro Phe Ala Leu Leu Tyr Val Leu Ser
                    1               5                   10 gtt tct ttc agg aaa atc ttc atc tta caa ctt gta ggg ctg gtg tta     280
Val Ser Phe Arg Lys Ile Phe Ile Leu Gln Leu Val Gly Leu Val Leu
            15                  20                  25 act tac gac ttc act aac tgt gac ttt gag aag att aaa gca gcc tat     328
Thr Tyr Asp Phe Thr Asn Cys Asp Phe Glu Lys Ile Lys Ala Ala Tyr
        30                  35                  40 ctc agt act att tct aaa gac ctg att aca tat atg agt ggg acc aaa     376
Leu Ser Thr Ile Ser Lys Asp Leu Ile Thr Tyr Met Ser Gly Thr Lys
    45                  50                  55 agt acc gag ttc aac aac acc gtc tct tgt agc aat cgg cca cat tgc     424
Ser Thr Glu Phe Asn Asn Thr Val Ser Cys Ser Asn Arg Pro His Cys
60                  65                  70                  75 ctt act gaa atc cag agc cta acc ttc aat ccc acc gcc ggc tgc gcg     472
Leu Thr Glu Ile Gln Ser Leu Thr Phe Asn Pro Thr Ala Gly Cys Ala
```

```
                    80                  85                  90
tcg ctc gcc aaa gaa atg ttc gcc atg aaa act aag gct gcc tta gct     520
Ser Leu Ala Lys Glu Met Phe Ala Met Lys Thr Lys Ala Ala Leu Ala
            95                  100                 105 atc tgg tgc cca ggc tat tcg gaa act cag ata aat gct act cag gca     568
Ile Trp Cys Pro Gly Tyr Ser Glu Thr Gln Ile Asn Ala Thr Gln Ala
        110                 115                 120 atg aag aag gtc aca acc aat aaa tgt ctg gaa caa gtg tca caa tta     616
Met Lys Lys Val Thr Thr Asn Lys Cys Leu Glu Gln Val Ser Gln Leu
    125                 130                 135 caa gga ttg tgg cgt cgc ttc aat cga cct tta ctg aaa caa cag taa     664
Gln Gly Leu Trp Arg Arg Phe Asn Arg Pro Leu Leu Lys Gln Gln
140                 145                 150 accatcttta ttatggtcat atttcacagc ccaaaataaa tcatctttat taagtaaaaa     724
aaaa                                                                  728

<210> SEQ ID NO 14
<211> LENGTH: 154
<212> TYPE: PRT
<213> ORGANISM: Homo sapiens

<400> SEQUENCE: 14

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Val Thr
        115                 120                 125

Thr Asn Lys Cys Leu Glu Gln Val Ser Gln Leu Gln Gly Leu Trp Arg
    130                 135                 140

Arg Phe Asn Arg Pro Leu Leu Lys Gln Gln
145                 150

<210> SEQ ID NO 15
<211> LENGTH: 728
<212> TYPE: DNA
<213> ORGANISM: Homo sapiens
<220> FEATURE:
<221> NAME/KEY: CDS
<222> LOCATION: (200)..(664)
<223> OTHER INFORMATION:

<400> SEQUENCE: 15
gcagccagaa agctctggag catcagggag actccaactt aaggcaacag catgggtgaa     60
taagggcttc ctgtggactg gcaatgagag gcaaaacctg gtgcttgagc actggcccct    120
aaggcaggcc ttacagatct cttacactcg tggtgggaag agtttagtgt gaaactgggg    180
tggaattggg tgtccacgt atg ttc cct ttt gcc tta cta tat gtt ctg tca    232
```

```
                Met Phe Pro Phe Ala Leu Leu Tyr Val Leu Ser
                 1               5                  10 gtt tct ttc agg aaa atc ttc atc tta caa ctt gta ggg ctg gtg tta    280
Val Ser Phe Arg Lys Ile Phe Ile Leu Gln Leu Val Gly Leu Val Leu
         15                  20                  25 act tac gac ttc act aac tgt gac ttt gag aag att aaa gca gcc tat    328
Thr Tyr Asp Phe Thr Asn Cys Asp Phe Glu Lys Ile Lys Ala Ala Tyr
             30                  35                  40 ctc agt act att tct aaa gac ctg att aca tat atg agt ggg acc aaa    376
Leu Ser Thr Ile Ser Lys Asp Leu Ile Thr Tyr Met Ser Gly Thr Lys
     45                  50                  55 agt acc gag ttc aac aac acc gtc tct tgt agc aat cgg cca cat tgc    424
Ser Thr Glu Phe Asn Asn Thr Val Ser Cys Ser Asn Arg Pro His Cys
 60                  65                  70                  75 ctt act gaa atc cag agc cta acc ttc aat ccc acc gcc ggc tgc gcg    472
Leu Thr Glu Ile Gln Ser Leu Thr Phe Asn Pro Thr Ala Gly Cys Ala
                 80                  85                  90 tcg ctc gcc aaa gaa atg ttc gcc atg aaa act aag gct gcc tta gct    520
Ser Leu Ala Lys Glu Met Phe Ala Met Lys Thr Lys Ala Ala Leu Ala
             95                 100                 105 atc tgg tgc cca ggc tat tcg gaa act cag ata aat gct act cag gca    568
Ile Trp Cys Pro Gly Tyr Ser Glu Thr Gln Ile Asn Ala Thr Gln Ala
         110                 115                 120 atg aag aag agg aca acc aat aaa tgt ctg gaa caa gtg tca caa tta    616
Met Lys Lys Arg Thr Thr Asn Lys Cys Leu Glu Gln Val Ser Gln Leu
     125                 130                 135 caa gga ttg tgg cgt cgc ttc aat cga cct tta ctg aaa caa cag taa    664
Gln Gly Leu Trp Arg Arg Phe Asn Arg Pro Leu Leu Lys Gln Gln
140                 145                 150 accatcttta ttatggtcat atttcacagc ccaaataaa tcatctttat taagtaaaaa    724
aaaa                                                               728

<210> SEQ ID NO 16
<211> LENGTH: 154
<212> TYPE: PRT
<213> ORGANISM: Homo sapiens

<400> SEQUENCE: 16

Met Phe Pro Phe Ala Leu Leu Tyr Val Leu Ser Val Ser Phe Arg Lys
 1               5                  10                  15

Ile Phe Ile Leu Gln Leu Val Gly Leu Val Leu Thr Tyr Asp Phe Thr
             20                  25                  30

Asn Cys Asp Phe Glu Lys Ile Lys Ala Ala Tyr Leu Ser Thr Ile Ser
         35                  40                  45

Lys Asp Leu Ile Thr Tyr Met Ser Gly Thr Lys Ser Thr Glu Phe Asn
     50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Thr
        115                 120                 125

Thr Asn Lys Cys Leu Glu Gln Val Ser Gln Leu Gln Gly Leu Trp Arg
    130                 135                 140

Arg Phe Asn Arg Pro Leu Leu Lys Gln Gln
145                 150
```

```
145                    150

<210> SEQ ID NO 17
<211> LENGTH: 159
<212> TYPE: PRT
<213> ORGANISM: Homo sapiens
<220> FEATURE:
<221> NAME/KEY: MISC_FEATURE
<222> LOCATION: (127)..(129)
<223> OTHER INFORMATION: "Xaa" is one or more amino acid that is not Arg
      or Lys.

<400> SEQUENCE: 17

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Xaa Xaa
        115                 120                 125

Xaa Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155

<210> SEQ ID NO 18
<211> LENGTH: 160
<212> TYPE: PRT
<213> ORGANISM: Homo sapiens
<220> FEATURE:
<221> NAME/KEY: MISC_FEATURE
<222> LOCATION: (130)..(130)
<223> OTHER INFORMATION: "Xaa" is one or more amino acid that is not Arg
      or Lys.

<400> SEQUENCE: 18

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110
```

```
Tyr Ser Glu Thr Gln Ile Asn Ala Thr Gln Ala Met Lys Lys Arg Arg
        115                 120                 125

Lys Xaa Arg Lys Val Thr Thr Asn Lys Cys Leu Glu Gln Val Ser Gln
    130                 135                 140

Leu Gln Gly Leu Trp Arg Arg Phe Asn Arg Pro Leu Leu Lys Gln Gln
145                 150                 155                 160

<210> SEQ ID NO 19
<211> LENGTH: 21
<212> TYPE: DNA
<213> ORGANISM: Homo sapiens

<400> SEQUENCE: 19
gtcgacgcca ccatgttccc t                                          21

<210> SEQ ID NO 20
<211> LENGTH: 28
<212> TYPE: DNA
<213> ORGANISM: Homo sapiens

<400> SEQUENCE: 20
atgaagaaga ggacaaccaa taaatgtc                                   28

<210> SEQ ID NO 21
<211> LENGTH: 28
<212> TYPE: DNA
<213> ORGANISM: Homo sapiens

<400> SEQUENCE: 21
gacatttatt ggttgtcctc ttcttcat                                   28

<210> SEQ ID NO 22
<211> LENGTH: 21
<212> TYPE: DNA
<213> ORGANISM: Homo sapiens

<400> SEQUENCE: 22
agcggccgct catttgtcgt c                                          21
```

MODIFIED HUMAN THYMIC STROMAL LYMPHOPOIETIN

CROSS-REFERENCE TO RELATED APPLICATIONS

This application hereby claims the benefit of U.S. provisional application Ser. No. 60/307,345, filed Jul. 23, 2001, the entire disclosure of which is relied upon and incorporated by reference.

FIELD OF THE INVENTION

The invention generally relates to recombinant protein expression. More specifically, the invention relates to modified human thymic stromal lymphopoietin (TSLP) polypeptides that are resistant to degradation in mammalian cell culture, polynucleotides sequences encoding modified TSLP polypeptides, and processes for the production and use of modified TSLP.

BACKGROUND OF THE INVENTION

Thymic stromal lymphopoietin (TSLP) is a growth factor integral to both B and T cell development and maturation. In particular, murine TSLP supports B lymphopoieses and is required for B cell proliferation. Murine TSLP is also critical in controlling the rearrangement of the T cell receptor-gamma (TCRγ) locus, and has a substantial stimulatory effect on thymocytes and mature T cells. See, for example, Friend et al., 1994, *Exp. Hematol.*, 22:321-328; Ray et al., 1996, *Eur. J. Immunol.*, 26:10-16; Candeias et al., 1997, *Immunology Letters*, 57:9-14.

TSLP possess cytokine activity similar to IL-7. For example, TSLP can replace IL-7 in stimulating B cell proliferation responses (Friend et al., supra). TSLP and IL-7 appear to mediate their lymphopoietic effects via distinct mechanisms. For example, IL-7 activates Janus family tyrosine kinases, including JAK1 and JAK3, and modulates the activity of the signal transducer and activator of transcription 5 (STAT5) protein. While TSLP modulates the activity of STAT5, it fails to activate any Janus family tyrosine kinase members (Levin et. al., 1999, *J. Immunol.* 162:677-683). Although TSLP and IL-7 mediate similar effects on target cells, they also appear to have distinct signaling pathways and likely some variation in their biologic response.

The known activities of TSLP in modulating the immune system, particularly in stimulating B and T cell proliferation, development, and maturation, makes this molecule an attractive therapeutic tool. The ability to produce large quantities of the active polypeptide is essential to commercial production of human TSLP. Production of recombinant polypeptides in a mammalian cell expression system is most commonly used for commercial human therapeutic applications.

Recombinant huTSLP polypeptide has been expressed in a number of different expression systems, including mammalian cell lines, as described in WO 00/29581. However, production of useful quantities of active huTSLP protein in mammalian cells has been difficult. In particular, huTSLP expression in mammalian cells often yields a degraded product. Alternative polynucleotide molecules and methods to achieve production of useful quantities of active huTSLP polypeptide are needed.

SUMMARY OF THE INVENTION

The amino acid sequence of human TSLP was found to contain a unique sequence of amino acids containing a furin cleavage site. Modifications of the polypeptide to inactivate the furin cleavage site, according to the present invention, provides modified protease resistant huTSLP polypeptides which are more stable when expressed in mammalian cell systems as compared with the unmodified TSLP polypeptides.

Modified, protease resistant human TSLP polypeptides of the invention include those having one or more amino acid sequence modifications that alters and inactivates the furin cleavage site RRKRK, as shown in Table 1 below, positioned at approximately amino acid residues 127-131 of SEQ ID NO: 4. Suitable modifications include amino acid substitutions, deletions, additions, or combinations of these, that alter the amino acid sequence RRKRK to disrupt the furin cleavage site pattern RXXR, in particular those that disrupt the pattern RX(R/K)R. Also included are polypeptides which are substantially similar in amino acid sequence to the modified huTSLP polypeptides, and fragments thereof, that retain at least one activity of native TSLP and are protease resistant. In one embodiment, the sequences RKRK or RKRKV have been deleted from the amino acid sequence of the huTSLP polypeptides.

The invention also provides polynucleotide molecules encoding the modified protease resistant huTSLP polypeptides discussed above. Polynucleotide molecules of the invention include those having an in-frame nucleic acid sequence modification that disrupts or otherwise deactivates the codons that encode the furin cleavage site RRKRK [SEQ ID NO: 6] positioned at amino acid residues 127-131 of SEQ ID NO: 4. Suitable modifications of the cleavage site includes in-frame nucleic acid substitutions, deletions, additions, or combinations of these, that alter the nucleic acid sequence that encodes RRKRK to disrupt the encoded furin cleavage site pattern RXXR, particularly RX(R/K)R. Embodiments include, for example, deletion mutants in which the nucleotide sequence AGG AGA AAA AGG AAA [SEQ ID NO: 5] encoding RRKRK, or the nucleotide sequence AGA AAA AGG AAA GTC [SEQ ID NO: 7] encoding an amino acid sequence RKRKV [SEQ ID NO: 8] have been deleted. Also included are polynucleotide molecules having sequences which are substantially similar to polynucleotide molecules encoding the modified TSLP polypeptides, and fragments thereof that retain at least one activity of native TSLP and are protease resistant.

The invention also provides additional forms of modified huTSLP polypeptides, including soluble forms and fusion proteins. For example, the fusion proteins of the invention include modified huTSLP polypeptides fused to heterologous proteins or peptides that confer a desired function, such as to facilitate purification, oligomerization, stability, secretion or identification of the polypeptide. A fusion protein of the invention can be produced, for example, from an expression construct containing a polynucleotide molecule encoding modified protease resistant huTSLP polypeptide in frame with a polynucleotide molecule encoding the heterologous protein.

The invention also provides vectors, plasmids, expression systems, host cells, and the like, containing a modified protease resistant huTSLP polynucleotide molecule. Genetic engineering methods for the production of modified huTSLP polypeptides of the invention include expression of the polynucleotide molecules in cell free systems, cellular hosts, in tissues, and in animal models, according to known methods.

The invention further includes compositions containing a substantially purified modified huTSLP polypeptide of the invention and an acceptable carrier. Preferred are pharmaceutical compositions adapted for administration to cells, tissues, or patients, that are useful to induce the activities of B cells and T cells in therapeutic treatment, for example, of immune deficiency disorders, viral infections, and bacterial infections.

These and various other features and advantages of the invention will be apparent from a reading of the following detailed description and a review of the appended claims.

BRIEF DESCRIPTION OF THE SEQUENCES

SEQ ID NO: 1 is a polynucleotide sequence encoding a murine TSLP (GenBank AF232937)

SEQ ID NO: 2 is the amino acid sequence of murine TSLP encoded by SEQ ID NO:1.

SEQ ID NO: 3 is a polynucleotide sequence encoding a human TSLP (GenBank AY037115)

SEQ ID NO: 4 is the amino acid sequence of a human TSLP encoded by SEQ ID NO:3.

SEQ ID NO: 5 is a polynucleotide sequence AGG AGA AAA AGG AAA, encoding a furin cleavage site RRKRK.

SEQ ID NO: 6 is the amino acid sequence RRKRK encoded by SEQ ID NO: 5.

SEQ ID NO: 7 is a polynucleotide sequence AGA AAA AGG AAA GTC, encoding an amino acid sequence RKRKV present in human TSLP but not murine TSLP.

SEQ ID NO: 8 is the amino acid sequence RKRKV encoded by SEQ ID NO: 7.

SEQ ID NO: 9 is a polynucleotide sequence encoding a modified human TSLP having one or more in-frame modifications to the sequence AGG AGA AAA AGG AAA that encodes the furin cleavage site RRKRK, resulting in deactivation of the encoded furin cleavage site.

SEQ ID NO: 10 is the amino acid sequence of the modified TSLP encoded by SEQ ID NO: 9.

SEQ ID NO: 11 is a polynucleotide sequence encoding a modified TSLP polypeptide having codons AGA AAA AGG AAA encoding amino acids RKRK deleted.

SEQ ID NO: 12 is the amino acid sequence of the modified TSLP polypeptide encoded by SEQ ID NO: 11.

SEQ ID NO: 13 is a polynucleotide sequence encoding a modified TSLP polypeptide having codons AGG AGA AAA AGG AAA encoding amino acids RRKRK deleted.

SEQ ID NO: 14 is the amino acid sequence of the modified TSLP polypeptide encoded by SEQ ID NO: 13.

SEQ ID NO: 15 is a polynucleotide sequence encoding a modified TSLP polypeptide having codons AGA AAA AGG AAA GTC encoding amino acids RKRKV deleted.

SEQ ID NO: 16 is the amino acid sequence of the modified TSLP polypeptide encoded by SEQ ID NO: 15.

SEQ ID NO: 17 is a modified human TSLP polypeptide.

SEQ ID NO: 18 is a modified human TSLP polypeptide.

SEQ ID NO: 19 is a PCR forward primer.

SEQ ID NO: 20 is a PCR forward primer.

SEQ ID NO: 21 is a PCR reverse primer.

SEQ ID NO: 22 is a PCR reverse primer.

DETAILED DESCRIPTION OF THE INVENTION

Definitions:

The following definitions are provided to facilitate understanding of certain terms used frequently herein and are not meant to limit the scope of the present disclosure.

"Amino acid" refers to any of the twenty standard $\alpha$-amino acids as well as any naturally occurring and synthetic derivatives. Modifications to amino acids or amino acid sequences can occur during natural processes such as post-translational processing, or can include known chemical modifications. Modifications include, but are not limited to: phosphorylation, ubiquitination, acetylation, amidation, glycosylation, covalent attachment of flavin, ADP-ribosylation, cross linking, iodination, methylation, and the like.

As used herein the term "antibody" refers to intact antibodies including polyclonal antibodies (see, for example *Antibodies: A Laboratory Manual*, Harlow and Lane (eds), Cold Spring Harbor Press, (1988)), and monoclonal antibodies (see, for example, U.S. Patent Nos. RE 32,011, 4,902,614, 4,543,439, and U.S. Pat. No. 4,411,993, and *Monoclonal Antibodies: A New Dimension in Biological Analysis*, Plenum Press, Kennett, McKearn and Bechtol (eds.) (1980)). The term "antibody" also refers to a fragment of an antibody such as F(ab), F(ab'), $F(ab')_2$, Fv, Fc, and single chain antibodies which are produced by recombinant DNA techniques or by enzymatic or chemical cleavage of intact antibodies. The term "antibody" also refers to bispecific or bifunctional antibodies, which are an artificial hybrid antibody having two different heavy/light chain pairs and two different binding sites. Bispecific antibodies can be produced by a variety of methods including fusion of hybridomas or linking of Fab' fragments. (See Songsivilai et al., *Clin. Exp. Immunol.* 79:315-321 (1990), Kostelny et al., *J. Immunol.* 148:1547-1553 (1992)). As used herein the term "antibody" also refers to chimeric antibodies, that is, antibodies having a human constant antibody immunoglobin domain is coupled to one or more non-human variable antibody immunoglobin domain, or fragments thereof (see, for example, U.S. Pat. No. 5,595,898 and U.S. Pat. No. 5,693,493). Antibodies also refers to "humanized" antibodies (see, for example, U.S. Pat. No. 4,816,567 and WO 94/10332), minibodies (WO 94/09817), and antibodies produced by transgenic animals, in which a transgenic animal containing a proportion of the human antibody producing genes but deficient in the production of endogenous antibodies are capable of producing human antibodies (see, for example, Mendez et al., *Nature Genetics* 15:146-156 (1997), and U.S. Pat. No. 6,300,129). The term "antibodies" also includes multimeric antibodies, or a higher order complex of proteins such as heterdimeric antibodies. "Antibodies" also includes anti-idiotypic antibodies including anti-idiotypic antibodies against an antibody targeted to the tumor antigen gp72; an antibody against the ganglioside GD3; or an antibody against the ganglioside GD2.

"Fe" or "Fe polypeptide" refers to polypeptides containing the Fc domain of an antibody. The "Fe domain" refers to the portion of the antibody that is responsible for binding to antibody receptors on cells. An Fe domain can contain one, two or all of the following: the constant heavy 1 domain ($C_H1$), the constant heavy 2 domain ($C_H2$), the constant heavy 3 domain ($C_H3$), and the hinge region. The Fe domain of the human IgG1, for example, contains the $C_H2$ domain, and the $C_H3$ domain and hinge region, but not the $C_H1$ domain. Truncated forms of such polypeptides containing the hinge region that promotes dimerization are also included. See, for example, C. A. Hasemann and J. Donald Capra, Immunoglobins: Structure and Function, in William E. Paul, ed.

"Antisense" refers to polynucleotide sequences that are complementary to target "sense" polynucleotide sequence.

"Cell targeting moiety" refers to any signal on a polypeptide, either naturally occurring or genetically engineered, used to target a polypeptide to a cell, polypeptide, polynucleotide, or innate material.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity can be partial, in which only some of the polynucleotides match according to base pairing, or complete, where all the polynucleotides match according to base pairing.

As used herein, the term "derivative" refers to a modified resistant TSLP polypeptides attached to at least one additional chemical moiety, or to at least one additional polypeptide to form covalent or aggregate conjugate such as glycosyl groups, lipids, phosphate, acetyl groups, or C-terminal or N-terminal fusion proteins and the like.

"Expression" refers to transcription and translation occurring within a host cell. The level of expression of a DNA molecule in a host cell can be determined on the basis of either the amount of corresponding mRNA that is present within the cell or the amount of DNA molecule encoded protein produced by the host cell (Sambrook et al., 1989, *Molecular cloning: A Laboratory Manual*, 18.1-18.88).

As used herein, the term "furin cleavage site" refers to an amino acid sequence recognized and cleaved by furin. In human TSLP, for example, a furin cleavage site has been identified within the sequence RRKRK. In general, the minimal cleavage site for furin is RXXR and more preferably, RX(R/K)R. (Nakayama 1997, *Biochem J* 327:625-35). The term "furin" refers to a calcium dependent serine protease is involved in the processing of a variety of proteins. Furin is known to cleave various proproteins, such as growth factor precursors, into biologically active proteins. Furin mRNA has been detected in all tissues and cell lines examined, suggesting that its activity is ubiquitous and not focused on any particular target group of proteins. Examples of preproteins cleaved by furin include various growth factors, growth factor receptors, plasma proteins involved in blood-clotting and complement cascades, matrix metalloproteinases, viral-envelope glycoproteins, and bacterial exotoxins.

As used herein, the term "modified TSLP polypeptides" or "modified huTSLP polypeptides" is used interchangeably with "furin resistant TSLP" or "protease resistant TSLP" and refers to any huTSLP polypeptide that has been modified to inactivate the furin cleavage site RXXR, and that also retains a TSLP activity, such as stimulation of B or T cell proliferation or development, or binding to TSLP receptors, as described, for example, in WO 00/29581, or in the Examples below. The term "modified TSLP polypeptides" also includes variants and fragments such as the extracellular domain, as well as derivatives such as fusion proteins.

"Fusion protein" refers to a protein having a heterologous polypeptide attached via recombinant DNA techniques. The fused heterologous polypeptide can provide a specific function, for example, to determine the location of the fusion protein in a cell, enhance the stability of the fusion protein, facilitate purification of the fusion protein, or target the protein to a desired antigen or cell. Examples of such fusion proteins include polypeptides fused to a portion of an immunoglobulin molecule, for example, an Fc fragment, polypeptides fused to a histidine tag, a growth factor, and the like, as described, in WO 00/29581.

"Genetically engineered" refers to any recombinant method used to create a eukaryotic host cell that expresses a protein of interest. Methods and vectors for genetically engineering host cells are well known; for example, various techniques are illustrated in *Current Protocols in Molecular Biology*, Ausubel et al., eds. (Wiley & Sons, New York, 1988, and quarterly updates). Genetic engineering techniques include, but are not limited to, expression vectors, targeted homologous recombination and gene activation (see, for example, U.S. Pat. No. 5,272,071 to Chappel) and transactivation by engineered transcription factors (see, for example, Segal et al., 1999, *Proc Natl Acad Sci USA* 96(6):2758-63).

"Homology" refers to a degree of complementarity between polynucleotides, where the degree of complementarity between polynucleotide molecules has significant effects on the efficiency and strength of hybridization between the polynucleotide molecules.

"Host cell" or "host cells" refers to cells established in ex vivo culture. It is a characteristic of host cells discussed in the present disclosure that they be capable of expressing furin resistant TSLP, as defined herein. Examples of suitable host cells useful for aspects of the present invention include, but are not limited to, mammalian cell lines. Specific examples of such cell lines include human embryonic kidney cells (293 cells), Chinese hamster ovary (CHO) cells (Puck et al., 1958, *Proc. Natl. Acad. Sci. USA* 60, 1275-1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), COS cells, and CV-1 cells.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid, and the G:C ratio within the polynucleotides.

"Inactivated" refers an activity that has been rendered nonfunctional. For example, a furin cleavage site in a polypeptide can be inactivated by modifying the amino acid sequence. Cleavage of the modified polypeptide in the presence of furin is reduced, and preferably is eliminated, as compared with the wild type polypeptide. Reduced or eliminated cleavage is demonstrated, for example, by a change in the cleavage products as compared to the cleavage products of the wild type.

"Isolated" refers to a polynucleotide or polypeptide that has been separated from at least one contaminant (polynucleotide or polypeptide) with which it is normally associated. For example, an isolated polynucleotide is in a context or in a form that is different from that in which it is found in nature.

As used herein, the term "huTSLP polypeptide" refers to a human TSLP polypeptide having the amino acid sequence set forth in SEQ ID NO: 4, or a variant or fragment of that polypeptide that retains at least one activity of a TSLP having SEQ ID NO: 4. A variant is a polypeptide which has an amino acid sequence that is substantially similar to the amino acid sequence of the unaltered protein, or a fragment thereof. For the purposes of the present invention, "substantially similar" to is at least about 80% identical to, preferably at least about 90% identical to, more preferably at least about 95%, more preferably at least about 98%, most preferably at least about 99% identical to the amino acid sequence of the unaltered protein, and which retains the activity of the unaltered polypeptide. Amino acid substitutions which are conservative substitutions unlikely to affect biological activity are considered identical for the purposes of this invention and include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and the reverse. (See, for example, Neurath et al., *The Proteins*, Academic Press, New York (1979)).

The percent identity may be determined by visual inspection and mathematical calculation, or by a comparison of two sequences using various computer programs used by those of skill in the art. For example, the percent identity of two sequences can be determined using the GAP computer program, based on the algorithm of Smith and Waterman, *Adv. Appl. Math.* 2:482-489 (1981), (available from the University of Wisconsin Genetics Computer Group (UWGCG), University Research Park, Madison, Wis.). The preferred default parameters for the GAP program include: (1) a scoring matrix, blosum62, as described by Henikoff and Henikoff *Proc. Natl. Acad. Sci. USA* 89:10915 (1992)); a gap weight of 12; (3) a gap length weight of 4; and (4) no penalty for end gaps. Other programs used by those skilled in the art of sequence comparison may also be used.

"Polynucleotide" refers to a sequence of nucleotides. The nucleotides are either a sequence of polyribonucleotides or polydeoxyribonucleotides, or a mixture of both. Examples of polynucleotides in the context of the present invention include single and double stranded DNA, single and double stranded RNA, and hybrid molecules that have both mixtures of single and double stranded DNA and RNA. Further, the polynucleotides of the present invention can include one or more modified nucleotide.

As used herein the term "protein" and "polypeptide" are used interchangeably and is considered to be any chain of at least ten amino acids linked by peptide bonds. Purification of a protein from contaminating proteins can be accomplished through any number of known techniques, including, ammonium sulfate or ethanol precipitation, anion or cation exchange chromatography, phosphocellulose chromatography, hydrophobic interaction chromatography, affinity chromatography, hydroxylapatite chromatography, and lectin chromatography. Various protein purification techniques are illustrated in Current Protocols in Molecular Biology, Ausubel et al., eds. (Wiley & Sons, New York, 1988, and quarterly updates).

"STAT5" refers to a member of the signal transducers and activators of transcription (STAT) family of transcription factors known to be activated by one or more JAK kinase, translocate to the nucleus, and participate in transcriptional regulation by binding to specific DNA sites. Techniques for determining STAT5 activity include DNA binding assays, STAT5 dependent reporter assays, $^{32}$P-labeling of STAT5, and the like, as illustrated in *Current Protocols in Molecular Biology*, Ausubel et al., eds. (Wiley & Sons, New York, 1988, and quarterly updates).

"Thymic stromal lymphopoietin" (TSLP) refers to a growth factor that stimulates the process of hematolymphoid development, as described, for example, in WO 00/29581, and Sims et al., 2000, *J. Exp. Med.* 192:671-680.

"Vector," "extra-chromosomal vector", or "expression vector" refers to a first polynucleotide molecule, usually double-stranded, which can have inserted into it a second polynucleotide molecule, for example a heterologous polynucleotide, such as a polynucleotide encoding furin resistant human TSLP. A heterologous polynucleotide may or may not be naturally found in the host cell, and can be one or more additional copy of a nucleic acid sequence naturally present in the host genome. The vector transports the foreign polynucleotide into a suitable host cell. Once in the host cell, the vector can be capable of integrating into the host cell chromosomes. The vector can also contain the necessary elements to select cells containing the integrated polynucleotide, as well as elements to promote transcription of mRNA from the transfected polynucleotide. Examples of vectors within the scope of the present invention include, but are not limited to, plasmids, bacteriophages, cosmids, retroviruses, and artificial chromosomes.

Unless otherwise stated, the techniques utilized can be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel (1991) Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109-128, ed. E. J. Murray, The Humana Press Inc., Clifton, N.J.).

TSLP Polypeptides

Thymic stromal lymphopoietin (TSLP) is a growth factor, a member of the cytokine family of lymphopoietic signaling factors that is integral to both B and T cell development and maturation. TSLP promotes B cell lymphopoiesis to the $B220^+/IgM^+$ immature B cell stage and induces the proliferation of the factor-dependent cell line NAG8/7. TSLP is involved in controlling the rearrangement of the T cell receptor-gamma (TCRγ) locus, and has a substantial stimulatory effect on thymocytes and mature T cells.

The biological activities of TSLP on B and T cells partially overlap with the activities of the cytokine, IL-7. For example, both TSLP and IL-7 co-stimulate thymocytes and mature T cells, sustain the NAG8/7 cell line, and support B lymphopoiesis in fetal liver cells. These overlapping functions likely result from the common use by the TSLP and IL-7 receptor complexes of the IL-7R alpha-chain. (Park et al., 2000, *J. Experimental Medicine,* 192(5):659-669; Levin et al., 1999, *J. Immunol.,* 162(2): 677-83; Isaksen et al., 1999, *J. Immunol.,* 163(11):5971-7). Blockage of the IL-7 receptor will likely block the activities of both IL-7 and TSLP.

IL-7, together with IL-15, is important for the development and function of immune cells, B and T cells. IL-7 aids the development of CD4 and CD8 T cells as well as for the proliferation and survival of naïve and memory CD4 T cells. IL-15 is important for the development of natural killer (NK) cells, and is involved in the development of memory CD8 cells but not memory CD4 cells.

Using an IL-15 knockout mouse model and an antibody directed against the IL-7 receptor alpha chain, it was determined that IL-7 but not IL-15 is required for the proliferation of naïve CD8 T cells, including OTI TgT cells and polyclonal CD 44 lo. Acute homeostasis driven proliferation (HDP) of memory CD8 T cells (OTI or polyclonal CD44 hi)

is delayed in IL-15 KO mice and by treatment of wild type mice with anti-IL-7 receptor monoclonal antibody. In the absence of IL-15 and inhibition of IL-7 receptor function, memory T cell proliferation is almost completely inhibited. Basal homeostatic proliferation of CD8 memory T cells is blocked in IL-15 KO mice. Treatment with anti-IL-7 receptor monoclonal antibody delayed proliferation in wild type mice. In the absence of IL-15 and under inhibition of IL-7 receptor function, survival of the T cells is affected. These results indicate that IL-7 and IL-15 are essential for the proliferation and survival of CD8 memory T cells. Because TSLP and IL-7 share overlapping functional activities on T cells via the IL-7 receptor, it is anticipated that TSLP also functions to promote the proliferation and survival of CD8 memory T cells. The memory T cell data indicates that TSLP is useful for obtaining long term immunity, and thus can be used as a vaccine adjuvant.

More particularly, TSLP supports the proliferation and differentiation of committed B220$^+$ B cell progenitors in vitro (Ray, et al., 1996, Eur. J. Immunol. 1996, 26:10-16). Cells incubated in the presence of either IL-7 or TSLP express cell surface markers characteristic of the pro-B cell stage of B cell differentiation. TSLP can replace IL-7 during the first 4-6 days of in vitro culture to support the progression of B cell progenitors from uncommitted bipotential precursors. TSLP can also substitute for IL-7 in supporting the sustained proliferative response exhibited by B cell progenitors from CBA/N mice. TSLP supports the expansion of B220$^+$ pre-B cells from either fetal liver or bone marrow for several days in vitro. TSLP also facilitates proliferation and differentiation of pre-B cells isolated from bone marrow up until the stage of becoming mitogen responsive in the presence of the stromal cell line S17.

TSLP facilitates the expansion and differentiation of B cell progenitors in vitro, and can replace IL-7 in supporting the development of B cells from B220$^+$ precursors as well as uncommitted bipotential progenitors in vitro. Techniques for stimulating B lineage and T lineage cell proliferation are well known (Ray et al., 1996 supra; Namikawa et al., 1996, Blood 87(5):1881-1890), as are techniques for expanding hematopoietic cells from sources such as umbilical cord blood and bone marrow (W. Piacibello, et al., 1997, Blood, 89(8):2644-2653). TSLP, alone or in combination with other cytokines, such as IL-7, can be used to control and amplify pluripotent stem cell renewal and expansion for cord blood or bone marrow transplantation.

Recombinant IL-7 has been used to reconstitute a patient's immune system following autologous bone marrow transplantation (Abdul-Hai et al., 1996, Experimental Hematology 24:1416-1422). IL-7 induces proliferation and differentiation of pre-B cells and immature thymocytes. TSLP induces similar proliferative effects on pre-B cells. Therefore, TSLP, alone or in combination with other cytokines or growth factors such as IL-7, can be used to stimulate hematopoietic cell proliferation and differentiation.

TSLP induces tyrosine phosphorylation of both isoforms of STAT5 (STAT5a and STAT5b), resulting in STAT5-DNA complex formation and transcription of the STAT5-responsive gene CIS, a feedback modulator of STAT5 (Levin et al., supra; Isaksen et al., supra). STAT5 has been extensively studied in STAT5-deficient mice. One or both forms of STAT5 plays a role in modulating the immune system, hematopoiesis, sexually dimorphic growth, mammary development, hair growth, deposition of adipose tissue, and pregnancy (Davey, et al., 1999, Am. J. Hum. Genet. 65:959-965). Many cases of freshly isolated human lymphoid leukemic cells have been shown to exhibit constitutive activation of STAT5 (Nosaka, et al. 1999, The EMBO Journal 18(17):4754-4765).

As one example of a STAT5 regulated activity, STAT5a and STAT5b are required for normal mammary gland growth and differentiation (Richer et al., 1998, J. Biol. Chiem. 273(47):31317-31326). STAT5a-deficient mice lack proliferative mammary lobulo-alveolar outgrowth, and the females are unable to lactate. STAT5b-deficient female mice have impaired mammary gland development.

TSLP appears to be a central actor in B and T cell development. TSLP proteins are useful in therapies and treatments targeted at stimulating the proliferation and maturation of B and/or T cells, for example in the treatment immune disorders, such as AIDS. Inhibition of TSLP expression, for example by an anti-TSLP antibody, or engagement of the TSLP receptor with a non-active TSLP fragment or inhibitory analog of TSLP, can inhibit B and T cell development and proliferation, and therapeutically useful, for example, in the treatment of autoimmune disease or in preventing rejection of organ transplant.

Human TSLP polypeptides are described in WO 00/29581. The amino acid sequence of one preferred embodiment of the full length human TSLP is given in SEQ ID NO: 4. Computer analysis predicts that the mature polypeptide sequence corresponds to amino acids 29 to 159 of SEQ ID NO: 4, while the signal peptide is thought to correspond to amino acids 1 through 28 of SEQ ID NO: 4, or alternatively amino acids 1 through 34 or 1 through 116. The huTSLP polypeptides may be membrane bound or soluble, secreted polypeptides. In one embodiment, the soluble polypeptide may include all or part of the extracellular domain, but lack the transmembrane region, which would cause retention of the polypeptide on a cell membrane. Human TSLP polypeptides include variants of the polypeptide encoded by SEQ ID NO:4 having at least 80% identity in amino acid sequence to SEQ ID NO:4 and retaining at least one TSLP function, as well as fragments thereof retaining a TSLP function.

Protease Resistance

The nucleic acid sequences encoding murine TSLP (GenBank accession number AF232937) and human TSLP (GenBank accession number AY037115) were disclosed in PCT application WO 00/29581. As described more fully in the Examples below, expression of human TSLP cDNA in mammalian cells often yields a degraded product.

In contrast to human TSLP, murine TSLP was not degraded when expressed in mammalian cells. The nucleic acid and amino acid sequences of human and murine TSLP were compared, and significant differences were found. In particular, the human nucleic acid sequence encodes a unique stretch of amino acids, 127-RRKRV-132, not present in the murine protein. Further analysis suggested that this unique stretch of amino acids contained a furin cleavage site, 127-RRKRK-131.

As more fully described in the Examples below, human TSLP protein overexpressed and isolated from mammalian cell cultures, when analyzed, for example, by electrophoresis, contains a number of polypeptides, shown as numerous bands on a gel. A prominent band in the mixture of proteins has a molecular weight of approximately 6 kD. The amino acid sequence of the 6 kD fragment corresponded to the C-terminal end of TSLP, suggesting a cleavage point at the furin cleavage site, RRKRK. This data provides direct evidence that degradation of human TSLP expressed in mammalian cells resulted from cleavage at the furin cleavage site.

The furin cleavage site is located about 8 residues before the start of a fourth helix of a four-helix bundle in the amino acid sequence of huTSLP thought to be required for activity. Truncation of huTSLP at this furin cleavage site produces a three-helix bundle cytokine, and also removes the last of the conserved cysteine residues shared between mouse and huTSLP that is thought to be involved in intramolecular disulfide bond formation. Accordingly, cleavage of huTSLP at the furin cleavage site is thought to remove a portion of the molecule that is required for biological activity.

In the present invention, a furin cleavage site in huTSLP has been identified, and modified to prevent furin cleavage of huTSLP. According to the invention, one or more of the codons encoding the furin cleavage site, RRKRK, is altered, for example, by site-directed mutagenesis, to prevent recognition of the cleavage site by furin. Preferably, one or more codons are altered to disrupt the cleavage site. Since the minimal furin recognition site is RXXR, any modification that disrupts the RXXR pattern in huTSLP is within the scope of the present invention.

Modified Human TSLP Polypeptides

Modified human TSLP polypeptides of the present invention includes polypeptides having the human TSLP amino acid sequence set forth in SEQ ID NO: 4, modified to deactivate the furin cleavage site RRKRK [SEQ ID NO: 6], as well as variants having an amino acid sequence that is substantially similar to the amino acid sequence of SEQ ID NO: 4, or fragments thereof, that are both resistant to furin cleavage and retain a functional activity of human TSLP.

For the purposes of the present invention, the term "substantially similar" refers to least about 80% identical to, preferably at least about 90% identical to, more preferably at least about 95% identical to, more preferably at least about 98% identical to, most preferably at least about 99% identical to the amino acid sequence of the unaltered protein, and which retain at least some degree of at least one activity of the unaltered polypeptide. Amino acid substitutions which are conservative substitutions unlikely to affect biological activity are considered identical for the purposes of this invention and include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and the reverse. (See, for example, Neurath et al., *The Proteins*, Academic Press, New York (1979)). Further information regarding phenotypically silent amino acid exchanges can be found in Bowie et al., 1999, *Science* 247:1306-1310).

Modifications suitable for inactivating the furin cleavage site includes amino acid substitutions, deletions, additions, or combinations of these, that alter the amino acid sequence RRKRK to disrupt the furin cleavage site pattern RXXR, particularly disrupting the pattern RX(R/K)R, (wherein R refers to arginine, K refers to lysine, and X refers to any amino acid). In one embodiment the sequence RKRK or RKRKV has been deleted in the modified TSLP polypeptides of the present invention.

Preferably, at least two amino acids within the furin cleavage site are altered to remove dibasic amino acids arginine or lysine that can be recognized by furin. For example, the modification can result in substitution of one or more dibasic amino acids with one or more neutral amino acid. The dibasic amino acids can also be deleted, or an insertion can be made within the 127-131 amino acid region of SEQ ID NO: 4 to disrupt the cleavage site.

In one embodiment, the modified TSLP polypeptides of the invention include deletions of one or more, preferably two or more of the amino acid residues 127-RRKRK-131 of SEQ ID NO: 4 to disrupt the RXXR furin cleavage pattern. For example, deletion of one arginine (R) results in the disrupted sequence RKRK or RRKK; deletion of two arginines results in the disrupted sequence KRK or RKK; deletion of three arginines results in the disrupted sequence KK. Modified TSLP polypeptides also include deletions of four or all five basic amino acids, for example, deleting RKRK, RRKR, or RRKRK in the amino acid positions 128-RKRK-131 or 128-RKRKV-132 of SEQ ID NO: 4.

In an alternative embodiment, the modified human TSLP polypeptides of the invention include amino acid substitutions in the human TSLP amino acid sequence, wherein one or more, and preferably two or more of the amino acid residues 127-RRKRK-131 are substituted with a different amino acid residue, disrupting the RXXR pattern. Preferably, one or more arginine and/or lysine is substituted with a non-basic, more preferably a neutral amino acid. By way of example, substitution of one arginine (R) results in the disrupted sequence RXKRK or RRKXK; substitution of two arginines results in the disrupted sequence XXKRK or XRKXK; substitution of three arginines results in the disrupted sequence XXKXK. Preferred is the substitution of all five basic amino acids resulting in the sequence XXXXX, wherein X is a non-basic amino acid, preferably a neutral amino acid.

The modified huTSLP polypeptides of the invention also include amino acid additions to the huTSLP amino acid sequence where one or more amino acid residues are inserted into the furin cleavage sequence 127-RRKRK-131, disrupting the RXXR pattern. For example, two or more amino acids can be inserted, such as in the sequence 127-RRZ$_n$KRK-131 where Z is not R or K, and n is not 1; one or more, and preferably two or more amino acids can be inserted between arginines, or the sequence 127-RZ$_n$RKRK-131, where Z is not R or K, and n is not 2; and the like. Preferably, n is 3, 4, or 5, and Z is a neutral amino acid.

| Exemplary Modified Human TSLP Polypeptides | | |
|---|---|---|
| FURIN SITE | | RXXR |
| Native | [SEQ ID NO:4] | .....ATQAMKK<u>RRKRK</u>VTTN..... |
| Modified* | [SEQ ID NO:10] | .....ATQAMKK<u>XXXXX</u>VTTN..... |
| Deletion 1 | [SEQ ID NO:12] | .....ATQAMKK<u>R....</u>VTTN..... |
| Deletion 2 | [SEQ ID NO:14] | .....ATQAMKK<u>.....</u>VTTN..... |
| Deletion 3 | [SEQ ID NO:16] | .....ATQAMKK<u>R....</u>VTTN..... |
| Substitution* | [SEQ ID NO:17] | .....ATQAMKK<u>XXXRK</u>VTTN..... |
| Addition** | [SEQ ID NO:18] | .....ATQAMKK<u>RRKZ.RK</u>VTTN..... |

X (*) can designate an amino acid substitution, deletion, insertion, or combination of these that disrupts the activity of the furin cleavage site.

In one exemplary embodiment, for example, set forth in SEQ ID NO: 10, all of the amino acids designated by X are modified to be any amino acid, preferably a neutral amino acid, other than R or K. In another embodiment, one or more, and preferably two or more of X is an amino acid deletion, most preferably two or more arginine (R) residues are deleted, and most preferably each X represents a deleted amino acid. In another embodiment, one or more, and preferably two or more of X is an amino acid substitution that is not K or R, and is preferably neutral amino acid. In this embodiment, XXXXX can be, for example, XRXRX, XRXRK, RXRXX, or RXRXK.

As set forth in SEQ ID NO: 18, Z(**) can be any amino acid that is not R or K, and preferably is a neutral amino acid. As discussed above, n can be any number that disrupts the RXXR pattern, for example, n can be 1 or greater, and preferably is 3, 4, or 5. Other exemplary methods for deactivating the furan cleavage site pattern RXXR and particularly RXR/KR will be apparent and are encompassed in the invention.

Examples of modified huTSLP polypeptides presented above include polypeptides having the amino acid sequences set forth in SEQ ID NO: 10, 12, 14, 16, 17, or 18, as well as polypeptides having an amino acid sequence which is substantially similar to these sequences, that is, having at least 80% identity to these amino acid sequences, and retaining resistance to furin cleavage as well as having at least one TSLP activity. Human TSLP polypeptide activity can be readily determined, for example, by subjecting a variant, derivative, or fragment of a human TSLP polypeptide to the BAF/HRT bioassay described in Example 3 below, or using the NAG8/7 cell proliferation assays as described by Friend et al., supra, or to STAT5 activation assays as described by Levin et al., supra.

The modified huTSLP polypeptides may be membrane bound or soluble, secreted polypeptides. In one embodiment, the soluble modified polypeptide may include all or part of the extracellular domain, but lack the transmembrane region, which would cause retention of the polypeptide on a cell membrane. Human TSLP polypeptides include variants of the polypeptide encoded by SEQ ID NO:4 having at least 80% identity in amino acid sequence to SEQ ID NO:4 and retaining at least one TSLP function, as well as fragments thereof such as the soluble domain retaining a TSLP function.

Useful derivatives of the modified polypeptides of the invention include, for example, modified human TSLP polypeptides attached to at least one additional chemical moiety, or to at least one additional heterologous polypeptide to form covalent or aggregate conjugate such as glycosyl groups, lipids, phosphate, acetyl groups, or C-terminal or N-terminal fusion proteins and the like. Preferred heterologous polypeptides include those that facilitate purification, stability, cellular or tissue targeting, or secretion of the modified human TSLP, such as fusion proteins with the Fc polypeptide.

Modifications of the amino acid sequence of human TSLP polypeptides can be accomplished by any of a number of known techniques. For example, mutations can be introduced at particular locations by known procedures such as oligonucleotide-directed mutagenesis (Walder et al., 1986, *Gene*, 42:133; Bauer et al., 1985, *Gene* 37:73; Craik, 1985, *BioTechniques*, 12-19; Smith et al., 1981, *Genetic Engineering: Principles and Methods*, Plenum Press; and U.S. Pat. No. 4,518,584 and U.S. Pat. No. 4,737,462).

The modified human TSLP polypeptides of the present invention are preferably provided in an isolated form, and preferably are substantially purified. The polypeptides can be recovered and purified from recombinant cell cultures by known methods, including ammonium sulfate or ethanol precipitation, anion or cation exchange chromatography, phosphocellulose chromatography, hydrophobic interaction chromatography, affinity chromatography, hydroxylapatite chromatography, and lectin chromatography. In a preferred embodiment, high performance liquid chromatography (HPLC) is employed for purification.

Modified human TSLP can be fused to heterologous regions used to facilitate purification of the polypeptide. Many of the available peptides (peptide tags) allow selective binding of the fusion protein to a binding partner. Non-limiting examples of peptide tags include 6-H is, thioredoxin, hemaglutinin, GST, and the OmpA signal sequence tag. A binding partner that recognizes and binds to the peptide can be any molecule or compound including metal ions (for example, metal affinity columns), antibodies, antibody fragments, and any protein or peptide, which binds the heterologous peptide to permit purification of the fusion protein.

Fragments spanning a modified furin cleavage site, including a fragment where the furin cleavage site has been deleted, can be used to generate specific antibodies against modified huTSLP polypeptides. The fragments should be short, between 5 and 20 amino acids, and preferably between 5 and 10 amino acids. Using known selection techniques, specific epitopes can be selected and used to generate monoclonal or polyclonal antibodies. Such antibodies have utility in the assaying protease resistant huTSLP activity, specifically identifying the expression of protease resistant huTSLP, and in the purification of the modified huTSLP from cell culture.

Modified TSLP Polynucleotide Sequences

The invention also provides isolated nucleic acid molecules which comprise polynucleotides encoding the modified huTSLP polypeptides of the present invention. Polynucleotides of the invention include those having an in-frame nucleotide sequence modification that disrupts or otherwise deactivates the codons that encode the furin cleavage site RRKRK [SEQ ID NO: 6] positioned at approximately amino acid residues 127-131 of SEQ ID NO: 4, such as, for example, the polynucleotide sequence AGG AGA AAA AGG AAA [SEQ ID NO: 5]. Suitable modifications include in-frame nucleic acid substitutions, deletions, additions, or combinations of these, that alter the sequence that encodes RRKRK to disrupt the encoded furin cleavage site pattern RXXR, particularly RX(R/K)R. For example, in one embodiment the sequence: AGA AAA AGG AAA GTC [SEQ ID NO: 7] encoding an amino acid sequence RKRKV [SEQ ID NO: 8] is deleted.

Exemplary Human TSLP Mutant Polynucleotides

| FURIN SITE | | K | K | R | R | K | R | K | V | T | T |
|---|---|---|---|---|---|---|---|---|---|---|---|
| Native | [SEQ ID NO:3] | AAG | AAG | AGG | AGA | AAA | AGG | AAA | GTC | ACA | ACC |
| Modified* | [SEQ ID NO:9] | AAG | AAG | xxx | xxx | xxx | xxx | xxx | GTC | ACA | ACC |
| Deletion 1 | [SEQ ID NO:11] | AAG | AAG | AGG | ... | ... | ... | ... | GTC | ACA | ACC |
| Deletion 2 | [SEQ ID NO:14] | AAG | AAG | ... | ... | ... | ... | ... | GTC | ACA | ACC |
| Deletion 3 | [SEQ ID NO:16] | AAG | AAG | ... | ... | ... | ... | ... | | ACA | ACC | x (*) can designate any in-frame nucleotide substitution, deletion, insertion, or combination of these, that disrupts the activity of the furan cleavage site.

In one exemplary embodiment set forth in SEQ ID NO: 9, each xxx encodes any amino acid except for R or K, preferably a neutral amino acid. In another embodiment, one or more, and preferably two or more codons xxx are deleted, most preferably two or more codons encoding arginine (R) residues are deleted, and most preferably each xxx represents a deleted codon. In another embodiment, one or more, and preferably two or more of x are nucleotide substitutions that do not form codons encoding K or R, and preferably encode neutral amino acids. In a further embodiment, one or more codons are inserted to disrupt the amino acid sequence of the furin cleavage site, as discussed above, for example, RRKZ$_n$RK. Other exemplary methods for modifying the codons to deactivate the furin cleavage site pattern RXXR and particularly RXR/KR will be apparent and are encompassed in the invention.

Therefore, modified huTSLP polynucleotides of the invention include polynucleotides having in-frame deletions, substitutions, or additions to SEQ ID NO: 3, as long as the addition, deletion, or substitution deactivates the cleavage site and encodes a furin resistant huTSLP polypeptide molecule which retains a TSLP activity. In addition, the polynucleotides of the invention encompasses polynucleotides having sequences which are substantially similar to this modified SEQ ID NO: 3, or a fragment of SEQ ID NO:3, and which encode modified TSLP polypeptides which retain both at least one TSLP activity and furin resistance.

As used herein, a nucleic acid molecule is "substantially similar to" another nucleic acid molecule if its polynucleotide sequence is at least 80% identical, preferably 90% identical, more preferably 95% identical, more preferably 98% identical, and most preferably 99% identical to the sequence of the second nucleic acid molecule, and if it encodes a modified TSLP polypeptide of the present invention retaining both a TSLP activity and furin resistance. Polynucleotide sequence identity is determined by known methods, for example by aligning two sequences in a software program such as the MACAW program created by Greg Schuler. In addition, the percent identity may be determined by visual inspection and mathematical calculation, or by comparing sequence information using the GAP computer program, version 6 described by Devereux et al. Nucl. Acids Res. 12:387 (1984), and available from the University of Wisconsin Genetics Computer Group (UWGCG).

The modified huTSLP polynucleotides of the present invention can be cDNA, chemically synthesized DNA, DNA amplified by PCR, RNA, or combinations thereof. Due to the degeneracy of the genetic code, two DNA sequences can differ and yet encode identical amino acid sequences. The present invention thus provides a nucleic acid molecule having a polynucleotide sequence encoding a modified huTSLP polypeptide. The nucleic acid molecules of the present invention having a polynucleotide sequence encoding a polypeptide which is substantially similar to SEQ ID NO: 4 and modified to inactivate the furin cleavage site RRKRK. As used herein, "substantially similar" refers to a polypeptide having at least 80% identity in amino acid sequence to the modified SEQ ID NO: 4, wherein the polypeptide retains both resistance for furin cleavage and a TSLP activity.

The present invention also includes polynucleotides having SEQ ID NO: 9, 11, 13, or 15 and polynucleotides which are substantially similar to these polynucleotide sequences. In addition, the present invention provides polynucleotides encoding the polypeptides of SEQ ID NO: 10, 12, 14, 16, 17, or 18, and polynucleotides encoding polypeptides which are substantially similar to these polypeptides.

Useful fragments of the polynucleotides of the invention include probes and primers. These can be used, for example, in PCR methods to amplify and detect the presence of modified huTSLP polynucleotides in vitro, as well as in Southern and Northern blots for analysis of protease resistant huTSLP. Cells transiently or stably overexpressing the protease resistant huTSLP polynucleotide molecules of the invention can also be identified by the use of such probes. Methods for the production and use of such primers and probes are known.

Other useful fragments include antisense or sense oligonucleotides comprising a single-stranded nucleic acid sequence capable of binding to a target modified huTSLP mRNA (using a sense strand) or DNA (using an antisense strand) sequence.

Vectors and Host Cells

The present invention provides vectors containing the polynucleotides described above, as well as host cells transformed with such vectors. Any of the polynucleotides molecules of the invention can be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the modified huTSLP polynucleotide molecule. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a modified huTSLP DNA sequence if the promoter nucleotide sequence directs the transcription of the modified TSLP sequence.

Selection of suitable vectors for the cloning of protease resistant huTSLP polynucleotide molecules of this invention will depend upon the host cell in which the vector will be transformed, and, where applicable, the host cell from which the target polypeptide is to be expressed. Suitable host cells include prokaryotes, yeast, and higher eukaryotic cells, each of which is discussed below. Modified huTSLP polypeptides are often expressed in mammalian cells.

The modified huSLP polypeptides to be expressed in host cells can also be a fusion proteins comprising the TSLP polypeptide and at least one heterologous polypeptide. As discussed above, heterologous polypeptides can be fused to the TSLP polypeptide to facilitate, for example, secretion, stability, purification, and/or targeting of the modified huTSLP polypeptide. Examples of fusions proteins provided by the present invention includes fusions of modified TSLP polypeptides with, for example Fc polypeptides and leucine zipper domains to promote the oligomerization of the TSLP polypeptides as described in WO 00/29581.

In another embodiment, a nucleotide sequence encoding an appropriate signal peptide can be incorporated into an expression vector. A nucleic acid sequence encoding a signal peptide (secretory leader) can be fused in-frame to the modified huTSLP sequence so that modified huTSLP is translated as a fusion protein comprising the signal peptide. A signal peptide that is functional in the intended host cell promotes extracellular secretion of the polypeptide. Preferably, the signal sequence will be cleaved from the modified huTSLP polypeptide upon secretion of the polypeptide from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells; most preferred are mammalian cells. Suitable prokaryotic hosts that can be used for the expression of these polypeptides include bacteria of the genera *Escherichia, Bacillus*, and *Salmonella*, as well as members of the genera *Pseudomonas, Streptomyces*, and *Staphylococcus*. For expression in prokaryotic cells, for example *E. coli*, the polynucleotide molecule encoding the modified huTSLP polypeptide preferably includes an N-terminal methionine residue to facilitate expression of the recombinant polypeptide. The N-terminal Met can optionally be cleaved from the expressed polypeptide.

Expression vectors for use in prokaryotic hosts generally comprise one or more phenotypic selectable marker gene. Such gene generally encodes, for example, a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

Modified huTSLP can also be expressed in yeast host cells from genera including *Saccharomyces, Pichia*, and *Kluveromyces*. Preferred yeast hosts are *S. cerevisiae*, and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) can also be used. In addition to the above-mentioned features of yeast vectors, a shuttle vector will also include sequences for replication and selection in *E. coli*. Direct secretion of the target polypeptides expressed in yeast hosts can be accomplished by the inclusion of nucleotide sequence encoding the yeast I-factor leader sequence at the 5' end of the modified huTSLP encoding nucleotide sequence.

Insect host cell culture systems can also be used for the expression of the modified huTSLP polypeptides. The target polypeptides of the invention are preferably expressed using a baculovirus expression system, as described, in a review by Luckow and Summers, 1988*, Bio/Technology* 6:47.

In the preferred embodiment, the modified huTSLP polypeptides of the invention are expressed in mammalian host cells. Non-limiting examples of suitable mammalian cell lines include the COS-7 line of monkey kidney cells (Gluzman et al., 1981, Cell 23:175), Chinese hamster ovary (CHO) cells (Puck et al., 1958, *Proc. Natl. Acad. Sci. USA,* 60:1275-1281; CV-1 cells (ATC CRL-10478); 293 cells, COS cells, and human cervical carcinoma cells (HELA) (ATCC CCL 2).

The choice of a suitable expression vector for expression of the target polypeptides of the invention will depend upon the specific mammalian host cell to be used. Examples of suitable expression vectors include pDC 409 (McMahan et al., 1991, *EMBO J.* 10:2821), pDC 317 (Source), pcDNA3.1/Hygro (Invitrogen), pSVL (Pharmacia Biotech) and the vectors described in WO 01/27299.

Expression vectors for use in mammalian host cells can include transcriptional and translational control sequences derived from viral genomes. Commonly used promoter sequences and enhancer sequences that can be used to express the modified human TSLP include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg, 1983*, Mol. Cell. Biol.* 3:280; Cosman et al., 1986, *Mol. Immunol.* 23:935; Cosman et al., 1984*, Nature* 312: 768; EP-A-0367566; and WO 91/18982.

Modification of a protease resistant huTSLP polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of modified human TSLP polypeptides include the expression of the polynucleotide molecules in cell free expression systems, in cellular hosts, in tissues, and in animal models, according to known methods.

Compositions

The invention provides compositions containing a substantially purified modified huTSLP polypeptide of the invention and a carrier. For therapeutic applications, the invention provides compositions adapted for pharmaceutical use, for example, containing a pharmaceutically acceptable carrier. Pharmaceutical compositions of the invention are administered to cells, tissues, or patients, for example, to induce the activity of B and T cells; and for therapeutic treatment, for example, in stimulating immune cell proliferation and development in immuno-suppressed patients, for example AIDS. The pharmaceutical compositions containing a modified huTSLP polypeptide are also useful as vaccine adjuvants, for example, useful for obtaining long-term immunity.

The invention also provides reagents, compositions, and methods that are useful for analysis of B and T cell activity; for analysis of STAT5 activity; and for analysis of the inhibitory/stimulatory effects of signal molecules involved in innate immune system responses.

Antibodies

The polypeptides of the present invention, in whole or in part, can be used to generate antibodies that are useful in assays for detecting modified huTSLP polypeptide expression and for purification of overexpressed modified human TSLP. Antibodies against modified TSLP polypeptides can be used as an antagonist to TSLP activity in a system. Methods for the selection of peptide epitopes and production of antibodies are known. See, for example, *Antibodies: A Laboratory Manual*, Harlow and Land (eds.), 1988 Cold Spring Harbor Laboratory Press, Cold Spring Harbor, N.Y.; *Monoclonal Antibodies, Hybridomas: A New Dimension in Biological Analyses*, Kennet et al. (eds.), 1980, Plenum Press, New York.

In addition to the production of antibodies, all or a portion of the modified TSLP polypeptide of the invention can be used, for example, as a targeting moiety to target binding to cells and tissues expressing TSLP receptors.

Assays

Human TSLP activity can be identified and measured using a number of assays including assays involving huTSLP effects on B and T cell proliferation and development. One such assay is described in Example 3. BAF cells expressing human TSLP receptors (BAF/HTR) which require active TSLP for proliferation can be used to measure TSLP activity as described in Example 3 herein. Additional assays for hTSLP activity include, for example, an assay measuring induction of T cell growth from human bone marrow by TSLP is described in WO 00/29581. Another TSLP activity is the ability to activate STAT5 as described in the reference to Levin et al., 1999, *J. Immunol.* 162:677-683, and in Example 4 herein.

These assays can be used to determine and quantitate on a relative basis TSLP activity, for various modified TSLP polypeptides including variants and derivates. In addition, these assays can be used identify agents which act to modify TSLP activity, or eliminate TSLP activity. For example, a lower modified huTSLP activated test activity in the presence of the test agent, compared with the absence of the test agent, indicates that the test agent has decreased the activity of the modified huTSLP. A higher protease resistant huTSLP activated test activity in the presence of the test agent than in the absence of the test agent indicates that the test agent has increased the activity of the protease resistant huTSLP. Stimulators and inhibitors of modified huTSLP can be used to augment, inhibit, or modify huTSLP mediated activity, and therefore can have therapeutic uses. For example, inhibitors of modified huTSLP can be useful to reduce B and T cell activity, for example in autoimmune diseases or in patients undergoing organ transplants.

Therapeutic Applications

The modified huTSLP polypeptides of the invention can be used therapeutically in the same manner known for the therapeutic use of the huTSLP polypeptide, as discussed in the publications referenced above. huTSLP is effective to stimulate B and T cell activities. For example, huTSLP, and preferably micromolar amounts of soluble modified huTSLP induces B and T cell differentiation, proliferation, and activation. Such administration is therapeutically useful in the treatment of bacterial and viral infections, as well as in the treatment of tumor cells and autoimmune deficiencies.

Further, the polypeptides of the present invention can be used alone or in combination with IL-7 to reconstitute a patient's immune system following autologous bone marrow transplantation (see for example Abdul-Hai et al., 1996, *Experimental Hematology*, 24:1416-1422). TSLP, due to its known effects on STAT5, can also be used in therapies targeted to modify STAT5 effects on a patient (see Richer et al., 1998, *J. Biol. Chem.*, 273(47):31317-31326; Davey et al., 1999, *Am. J. Hum. Genet.*, 65:959-965; Nosaka et al., 1999, *EMBO J,* 18(17):4754-4765).

Modified human TSLP polynucleotides and polypeptides, including vectors expressing modified huTSLP, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and can be combined with or conjugated to specific delivery agents, including targeting antibodies and/or cytokines.

Modified human TSLP can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection. In one embodiment of the invention, the compounds can be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions can also be prepared in glycerol, liquid polyethylene, glycols, DNA, vegetable oils, triacetin and mixtures thereof. Under ordinary conditions of storage and use, these preparations can contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption, for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Having generally described the invention, the same will be more readily understood by reference to the following examples, which are provided by way of illustration and are not intended as limiting.

EXAMPLES

Example 1

Recognition and Modification of Furin Cleavage Site

The nucleic acid sequences encoding murine TSLP (GenBank accession number AF232937) [SEQ ID NO: 3] and human TSLP [SEQ ID NO: 5] were disclosed in PCT application WO 00/29581. Production of useful quantities of human TSLP cDNA in mammalian cells is hampered, however, as expression in mammalian cells often yields a degraded product.

Expression of human recombinant TSLP in mammalian cells provided substantially lower quantities of full length recombinant protein than expected. A portion the expressed protein was in a cleaved, fragmented form, having a major degradation product of 6 kD. In contrast to human TSLP, murine TSLP was not degraded when expressed in mammalian cells. The nucleic acid and amino acid sequences of the human and murine TSLP were then compared. As shown in Table 1, comparison of the human TSLP amino acid sequence with a murine TSLP amino acid sequence revealed a series of residues, beginning at residue 128, found exclusively in the human TSLP (128-RKRKV-132). Upon further investigation, it was determined that the residues represented a furin cleavage site (127-RRKRK-131). Importantly, the position of the furin cleavage site correlated with release of an approximate 6 kD C-terminal fragment of human TSLP.

The huTSLP amino acid sequence includes an N-terminal hydrophobic region that functions as a signal peptide followed by a series of 4 helixes forming a four-helix bundle cytokine structure. The furin cleavage site is positioned about 8 amino acids before the start of the fourth helix of the four-helix bundle. Truncation of the protein at the cleavage site can result in an inactivated human TSLP protein.

TABLE 1

Comparison of murine and human TSLP polypeptides

| | | | |
|---|---|---|---|
| Human | 1 | MFPFALLYVLSVSFRKIFILQ.LVGLVLTYDFTNCDFEKIKAAYLSTISK | 49 |
| Mouse | 1 | MVLLRSLFILQVLVRMGLTYNFSNCNFTSITKIYCNIIFH | 40 |
| Human | 50 | DLITYMSGTKSTEFNNTVSCSNRPHCLTEIQSLTFNPTAGCASLAKEMFA | 99 |
| Mouse | 50 | DLTGDLKGAK...FEQIEDCESKPACLLKIEYYTLNPIPGCPSLPDKTFA | 87 |
| Human | 100 | MKTKAALAIWCPGYSETQIN.ATQAMKKRRKRKVTTNKCLEQVSQLQGLWR | 148 |
| Mouse | 100 | RRTREALNDHCPGYPETERNDGTQEMAQE.....VQNICLNQTSQILRLW | 132 |

TABLE 1-continued

Comparison of murine and human TSLP polypeptides

Human 150 RFNRPLLKQQ [SEQ ID NO: 4]
Mouse 150 YSFMQSPE   [SEQ ID NO: 2]

When TSLP protein is expressed and isolated from mammalian cell cultures, and analyzed, for example, by electrophoresis, a number of polypeptides result, shown as numerous bands on a gel. The most prominent band in the mixture of proteins has a molecular weight of approximately 6 kD. The amino acid sequence of the 6 kD fragment corresponds to the C-terminal end of TSLP, suggesting a cleavage point at the furin cleavage site, RRKRK. This data provides direct evidence that degradation of human TSLP expressed in mammalian cells results from cleavage at the furin cleavage site.

Example 2

Mutagenesis of Furin Site in Human TSLP

Site directed mutagenesis was used to inactivate the furin cleavage site from the human TSLP poly-H is FLAG transcript, using 313-human-TSLP His-FLAG (#14095) (1 mg/ml) as the template. A series of polymerase chain reaction (PCR) reactions was used to delete the nucleotide sequence: AGA AAA AGG AAA GTC [SEQ ID NO: 7] that encodes the huTSLP segment containing the furin cleavage site: RKRKV [SEQ ID NO: 8]. In addition, a combination of primers was designed to create a Sal-1 restriction site at the 5' end and a Not-1 site at the 3' end. The primers were as follows:

1. Forward (Sal-1): 5'-GTCGACGCCACCATGTTCCCT-3' [SEQ ID NO:19]

2. Forward: 5'-ATGAAGAAGAGGACAACCAATAAATGTC-3' [SEQ ID NO:20]

3. Reverse: 5'-GACATTTATTGGTTGTCCTCTTCTTCAT-3' [SEQ ID NO:21]

4. Reverse (Not-1): 5'-AGCGGCCGCTCATTTGTCGTC-3' [SEQ ID NO:22]

The polynucleotide sequence of human TSLP is shown below:

| HUMAN TSLP (GenBank AY037115) |
|---|
| 1 gcagccagaa agctctggag catcaggag actccaactt aaggcaacag catgggtgaa |
| 61 taagggcttc ctgtggactg gcaatgagag gcaaaacctg gtgcttgagc actggcccct |
| 121 aaggcaggcc ttacagatct cttacactcg tggtgggaag agtttagtgt gaaactgggg |
| 181 tggaattggg tgtccacgta tgttcccttt tgccttacta tatgttctgt cagtttcttt |
| 241 caggaaaatc ttcatcttac aacttgtagg gctggtgtta acttacgact tcactaactg |
| 301 tgactttgag aagattaaag cagcctatct cagtactatt tctaaagacc tgattacata |
| 361 tatgagtggg accaaaagta ccgagttcaa caacaccgtc tcttgtagca atcggccaca |
| 421 ttgccttact gaaatccaga gcctaacctt caatcccacc gccggctgcg cgtcgctcgc |
| 481 caaagaaatg ttcgccatga aaactaaggc tgccttagct atctggtgcc caggctattc |
| 541 ggaaactcag ataaatgcta ctcaggcaat gaagaagagg agaaaaagga aagtcacaac |
| 601 caataaatgt ctggaacaag tgtcacaatt acaaggattg tggcgtcgct tcaatcgacc |
| 661 tttactgaaa caacagtaaa ccatctttat tatggtcata tttcacagcc caaaataaat |
| 721 catctttatt aagtaaaaaa aaa [SEQ ID NO: 3] |

A PCR product of 409 bases was formed using primers 1 and 3 in a first PCR reaction. Primer 1 includes a Sal-1 restriction site, while primer 3 deletes the 15 base furin cleavage sequence. A second PCR product of 162 bases was formed using primers 2 and 4 in a second PCR reaction, with primer 4 includes a NOT-1 restriction site, while primer 2 deletes the 15 base furin cleavage site.

The PCR reactions contained 10 Tl of Amplitaq 10× buffer; 1Tl Amplitaq; 2Tl dNTPs (10 µM each); 40 µM each primer; 1Tl template; water to a final volume of 100Tl. The PCR was performed on a Perkin Elmer-Gene Amp PCR Systems 2400 machine, at: 1 cycle of 94° C., 2:00 minutes; 30 cycles of 94° C., 0:30 minutes, 50° C., 0:15 minutes, and 72° C., 1:00 minute; and one cycle of 72° C., 2:00 minutes.

PCR products were purified in 1% low melt agarose gels. Appropriate sized-bands were excised from the gel and the DNA was purified using a High Pure PCR Product Purification Kit obtained from Boehringer Mannheim. The gel-purified 409 and 162 base products were combined with primers 1 and 4 to produce a 558 base pair PCR product that contained the full length human TSLP polyHis-FLAG sequence lacking the base pair region encoding the furin cleavage site.

The reaction solution contained: 10Tl Amplitaq 10× buffer; 1Tl Amplitaq; 2Tl (10 pM each) dNTP; 15.4Tl (40 µM) Primer 1; 16 Tl (40 µM) Primer 4; 1Tl (41 ng) PCR Product A; 2Tl (119 ng) PCR Product B; and water to a final volume of 100 Tl. As above, the PCR reaction/conditions were carried out in the Perkin Elmer-Gene Amp PCR Systems 2400 machine. At the end of the reaction, the 558 base pair product was separated on a 1% low-melt agarose gel and purified.

Purified modified human TSLP sequence was ligated into vector pGEM-T (Promega), using the reagents supplied with the vector kit: 1Tl pGEM-T vector; 5Tl 2×ligation buffer; 1Tl ligase; and 1Tl 558 base pair modified human TSLP (12 ng). The reaction solution was left at room temperature for one hour. The ligation mixture (2Tl) was combined with 40 Tl of DH10I-electrocompetent E. coli, and electroporated into the bacteria. The electroporated bacteria were then transferred to 0.9 ml of SOC solution and shaken for one hour at 37° C.

A volume of 0.1Tl of this solution was spread on ampicillin-resistant plates and incubated at 37° C. overnight. Colonies were picked and inoculated into 4 mL of LB broth containing ampicillin. After overnight incubation on a shake platform at 37° C., the plasmid DNA was purified and digested with NOT-1/Sal-1 to confirm the correct size of the insert. The pGem-T vector with the 558 base pair insert was sequenced to confirm that the molecular manipulations had produced the desired mutation.

pGEM-T vector was digested with Not-1 and Sal-1, and the 558 base pair insert subcloned into expression vectors pDC 409 and pDC317. Digestion and ligation reactions were performed as is well known in the art. Expression vectors were then used to produce either transiently transfected CV-1 cells (ATCC CRL-10478) or to make stably expressing CHO cells. Note that for comparison, a control expression vector encoding human TSLP having an intact furin cleavage site was used to produce both transient and stable transfected cells.

HuTSLP and modified huTSLP protein were each expressed in CV-1 cells as a H'IS, Flag fusion protein. The expressed protein was purified using IMAC (immobilized metal affinity chromatography, using the manufacturer's instructions (Qiagen)). Analysis of the expressed protein on SDS-PAGE under reducing and non-reducing conditions demonstrated the production of modified huTSLP.

The constructed, modified human TSLP sequence, having the furin cleavage site removed, was expressed as full-length human TSLP protein in mammalian culture (CV-1 cells). When compared to the non-modified human TSLP, little or no degradation product was produced with expression of the furin-site deleted TSLP, demonstrating that the furin site was, in fact, the site responsible for the fragmentation of recombinant human TSLP.

Example 3

Active Modified Human TSLP

The activity of the modified huTSLP, produced as described for Example 2, was verified using a BAF/HRT cell bioassay. The BAF/HTR bioassay utilizes a murine pro B lymphocyte cell line, which has been transfected with the human TSLP receptor (cell line obtained from Steven F. Ziegler, Virginia Mason Research Center, Seattle, Wash.). The TSLPR DNA sequence was deposited with Genbank, (accession number AF201963) and is described in Pandey et al., 2000, Nat Immun 1(1), 59-64. These cells are dependent upon huTSLP for growth, and proliferate in a dose-dependent manner in response to active huTSLP added in test samples.

Titrations of samples and standards were performed in a 96-well microtiter format. A baseline quantity of BAF/HRT cells were added to each well. Samples of modified huTSLP and standards were added to the wells. Following an incubation period, cell proliferation was measured by the addition of Alamar Blue dye I (Biosource International Catalog #DAL1100, 10 uL/well). Metabolically active BAF/HRT cells take up and reduce Alamar Blue, which leads to change in the fluorescent properties of the dye. The number of fluorescent units produced in this assay by the modified, protease resistant huTSLP was similar to that of the reference unmodified huTSLP, showing that the modified huTSLP was equally active to unmodified huTSLP.

Example 4

Modified huTSLP Activates STAT5

The ability of modified huTSLP of the invention to activate STAT5 is analyzed according to the method described in Levin et al., 1999 supra. Briefly, NAG8/7 cells are cytokine starved for 4-5 hours, then stimulated at $10^7$ cells/ml with 100 ng/ml modified human TSLP. Unmodified huTSLP is used as a control. Post incubation, cells are harvested, washed, and lysed. Stimulated cell lysates are analyzed by immunoblot assay, and demonstrate modified huTSLP activity when compared with control.

The invention is described herein with reference to specific examples. Various changes and modifications can be made to these examples that are well within the scope of the invention. Numerous other changes can be made that are readily suggested to those skilled in the art and that are encompassed in the spirit of the invention disclosed herein and as defined in the appended claims.

All publications cited herein are hereby incorporated by reference.

We claim:

1. An isolated protein comprising a modified human thymic stromal lymphopoietin (TSLP) polypeptide, wherein the polypeptide is selected from the amino acid sequences consisting of SEQ ID NO: 10, 12, 14, 16, 17 and 18.

2. The protein of claim 1 wherein the polypeptide is fused to a heterologous protein.

3. The protein of claim 2, wherein the heterologous protein is a cell-targeting moiety.

4. The protein of claim 3, wherein the cell-targeting moiety is an antibody that binds a cell surface antigen.

5. The protein of claim 3, wherein the cell-targeting moiety is a ligand that binds a cell surface receptor.

6. The protein of claim 2, wherein the heterologous protein is a peptide tag.

7. The protein of claim 2, wherein the heterologous protein is an Fc polypeptide.

* * * * *

UNITED STATES PATENT AND TRADEMARK OFFICE
CERTIFICATE OF CORRECTION

PATENT NO. : 7,288,633 B2  
APPLICATION NO. : 10/202699  
DATED : October 30, 2007  
INVENTOR(S) : Stewart D. Lyman et al.

Page 1 of 1

It is certified that error appears in the above-identified patent and that said Letters Patent is hereby corrected as shown below:

In the Claims

Col. 48, line 50

Claim 7, line 2: "Fe polypeptide" should read  -- Fc polypeptide --.

Signed and Sealed this  
Twenty-sixth Day of November, 2013

Margaret A. Focarino  
*Commissioner for Patents of the United States Patent and Trademark Office*